United States Patent
Fong et al.

(10) Patent No.: US 8,017,822 B2
(45) Date of Patent: Sep. 13, 2011

(54) INTEGRATED PROCESS TO COPRODUCE AROMATIC HYDROCARBONS AND ETHYLENE AND PROPYLENE

(75) Inventors: Howard Lam Ho Fong, Sugar Land, TX (US); Richard Dale Swain, Houston, TX (US)

(73) Assignee: Shell Oil Company, Houston, TX (US)

( * ) Notice: Subject to any disclaimer, the term of this patent is extended or adjusted under 35 U.S.C. 154(b) by 86 days.

(21) Appl. No.: 12/573,767

(22) Filed: Oct. 5, 2009

(65) Prior Publication Data

US 2010/0087686 A1 Apr. 8, 2010

Related U.S. Application Data

(60) Provisional application No. 61/103,360, filed on Oct. 7, 2008.

(51) Int. Cl.
*C07C 1/26* (2006.01)
(52) U.S. Cl. ........ 585/408; 585/322; 585/641; 585/642; 568/795; 568/796; 568/797; 568/798; 568/802
(58) Field of Classification Search ........................ None
See application file for complete search history.

(56) References Cited

U.S. PATENT DOCUMENTS

| | | | |
|---|---|---|---|
| 4,795,843 A | 1/1989 | Imai et al. | 585/408 |
| 7,244,867 B2 | 7/2007 | Waycuilis | 585/408 |
| 2005/0234276 A1 | 10/2005 | Waycuilis | 585/310 |
| 2007/0238909 A1 | 10/2007 | Gadewar et al. | 585/16 |

OTHER PUBLICATIONS

LPG. Datasheet [online] Sinopec, Jul. 12, 2008 [retrieved on Apr. 22, 2010]. Retrieved from the Internet: RL:http://web.archive.org/web/20080712164323/http://english.sinopec.com/products_service/lpg/ p. 1, para [0001].

*Primary Examiner* — Brian J Davis

(57) ABSTRACT

An integrated process for producing aromatic hydrocarbons and ethylene and/or propylene and optionally other lower olefins from low molecular weight hydrocarbons, preferably methane, which comprises: (a) contacting at least one low molecular weight alkane, preferably methane, with a halogen, preferably bromine, under process conditions sufficient to produce a monohaloalkane, preferably monobromomethane, (b) reacting the monohaloalkane in the presence of a coupling catalyst to produce aromatic hydrocarbons and $C_{2+}$ alkanes, (c) separating the aromatic hydrocarbons from the product mixture of step (b) to produce aromatic hydrocarbons, and (d) cracking at least part of the $C_{2+}$ alkanes in an alkane cracking system to produce ethylene and/or propylene and optionally other lower olefins.

19 Claims, 1 Drawing Sheet

US 8,017,822 B2

INTEGRATED PROCESS TO COPRODUCE AROMATIC HYDROCARBONS AND ETHYLENE AND PROPYLENE

CROSSREFERENCE TO RELATED APPLICATION

This application claims priority to U.S. Provisional Application Ser. No. 61/103,360 filed Oct. 7, 2008, the entire disclosure of which is hereby incorporated by reference.

FIELD OF THE INVENTION

This invention relates to a process for the production of aromatic hydrocarbons by bromination of low molecular weight alkanes, particularly methane. More particularly, the invention relates to a process wherein aromatic hydrocarbons and ethylene and/or propylene are coproduced.

BACKGROUND OF THE INVENTION

U.S. Pat. No. 7,244,867 describes a process for converting lower molecular weight alkanes, including methane, natural gas or ethane, propane, etc., into higher molecular weight hydrocarbons, including aromatics, by bromination to form alkyl bromides and hydrobromic acid which are then reacted over a crystalline alumino-silicate catalyst to form the higher molecular weight hydrocarbons and hydrobromic acid. Hydrobromic acid is recovered by contacting the reaction product stream with water and then converted to bromine for recycle. The higher molecular weight hydrocarbons are recovered.

In a process for producing aromatic hydrocarbons such as benzene, toluene and/or xylenes (BTX) by bromination of methane to produce monobromomethane, followed by coupling of the monobromomethane to produce aromatic hydrocarbons, the coupling reactor produces hydrogen bromide (HBr), and unintended amounts of methane, light ends ($C_{2-5}$ alkanes and alkenes) and heavy ends ($C_{9+}$ aromatic hydrocarbons and possibly higher carbon number nonaromatic hydrocarbons). The basic process concept includes recycle of the light ends, possibly to a separate bromination reactor, and the use of methane and heavy ends as fuel. The light ends are more easily brominated than methane and if the bromination reaction of the light ends was to be carried out in the same bromination reactor a significant portion of the light ends would be converted to higher brominated species (e.g., dibromoethane, tribromopropane, etc.). Even in a separate light ends bromination reactor, it would be impossible to effect high conversion of ethane, propane and/or butanes without over-brominating because the rate of bromination increases with increasing carbon number. Further, alkenes present in the light ends stream will be brominated to alkyl dibromides regardless of the light ends bromination configuration. The multi-brominated light end derivatives decrease bromine efficiency and are more prone to coke formation in the coupling reactor than monobromomethane. The formation of coke represents a yield loss and the necessity of frequent burning off coke increases the carbon dioxide footprint of the process and reduces process reliability. If multi-brominated light ends were separated, it would create a stream with a high concentration of compounds suspected of being considerably more toxic than monobromomethane.

It can be seen that it would be advantageous to provide an integrated process concept wherein the light ends and heavy ends could be converted into useful products. The present invention provides such an integrated process.

SUMMARY OF THE INVENTION

The present invention provides an integrated process for producing aromatic hydrocarbons and ethylene and/or propylene, and optionally other lower olefins, from low molecular weight alkanes, preferably methane, which comprises:

(a) contacting one or more low molecular weight alkanes, preferably methane, with a halogen, preferably bromine, under process conditions sufficient to produce a monohaloalkane, preferably monobromomethane, (b) reacting the monohaloalkane in the presence of a coupling catalyst to produce aromatic hydrocarbons and $C_{2+}$, usually $C_{2-5}$, alkanes, (c) separating the aromatic hydrocarbons from the product mixture of step (b) to produce aromatic hydrocarbons, and (d) cracking at least part of the $C_{2+}$ alkanes in an alkane cracking system to produce ethylene and/or propylene and optionally other olefins such as butenes, pentenes, etc.

In an embodiment, $C_{4+}$ alkanes and alkenes which are co-produced may be separated from the $C_{2-3}$ alkanes and alkenes before step (d) or sent to step (d). The $C_{2-3}$ alkanes may be separated from $C_{2-3}$ alkenes and the $C_{2-3}$ alkanes may be cracked in step (d).

In another embodiment, $C_{9+}$ hydrocarbons, mostly $C_{9+}$ aromatics (the process typically produces less than 1% $C_{6+}$ nonaromatics) may also be produced in step (b) and may be separated from the other products of step (b), hydrogenated and then subjected to hydrocarbon cracking to produce olefins and/or aromatic hydrocarbons. At least part of the hydrogen used for the hydrogenation of the $C_{9+}$ hydrocarbons may be produced in (d).

In another embodiment, aromatic $C_{9+}$ hydrocarbons produced in step (b) may be separated and reproportionated with toluene to produce xylenes and/or hydrodealkylated to produce benzene, toluene and/or xylenes.

In another embodiment, at least some unconverted methane and/or at least some of any produced methane may be recovered and recycled to step (a). In another embodiment, at least some ethane and/or propane produced in step (b) may be recycled to step (a). In another embodiment, multi-brominated methane species from step (a) may be separated from the monobromomethane prior to step (b) and may be recycled to step (a).

In an embodiment, hydrogen bromide is produced in the process and at least some of the hydrogen bromide so produced may be converted to bromine which may be recycled to step (a). In another embodiment, hydrogen bromide (HBr) is produced in the bromination step and may be removed prior to the coupling step. In another embodiment, at least some HBr is present in the $C_{2+}$ alkanes stream and may be removed therefrom prior to step (d).

DETAILED DESCRIPTION OF THE INVENTION

Figure 1:
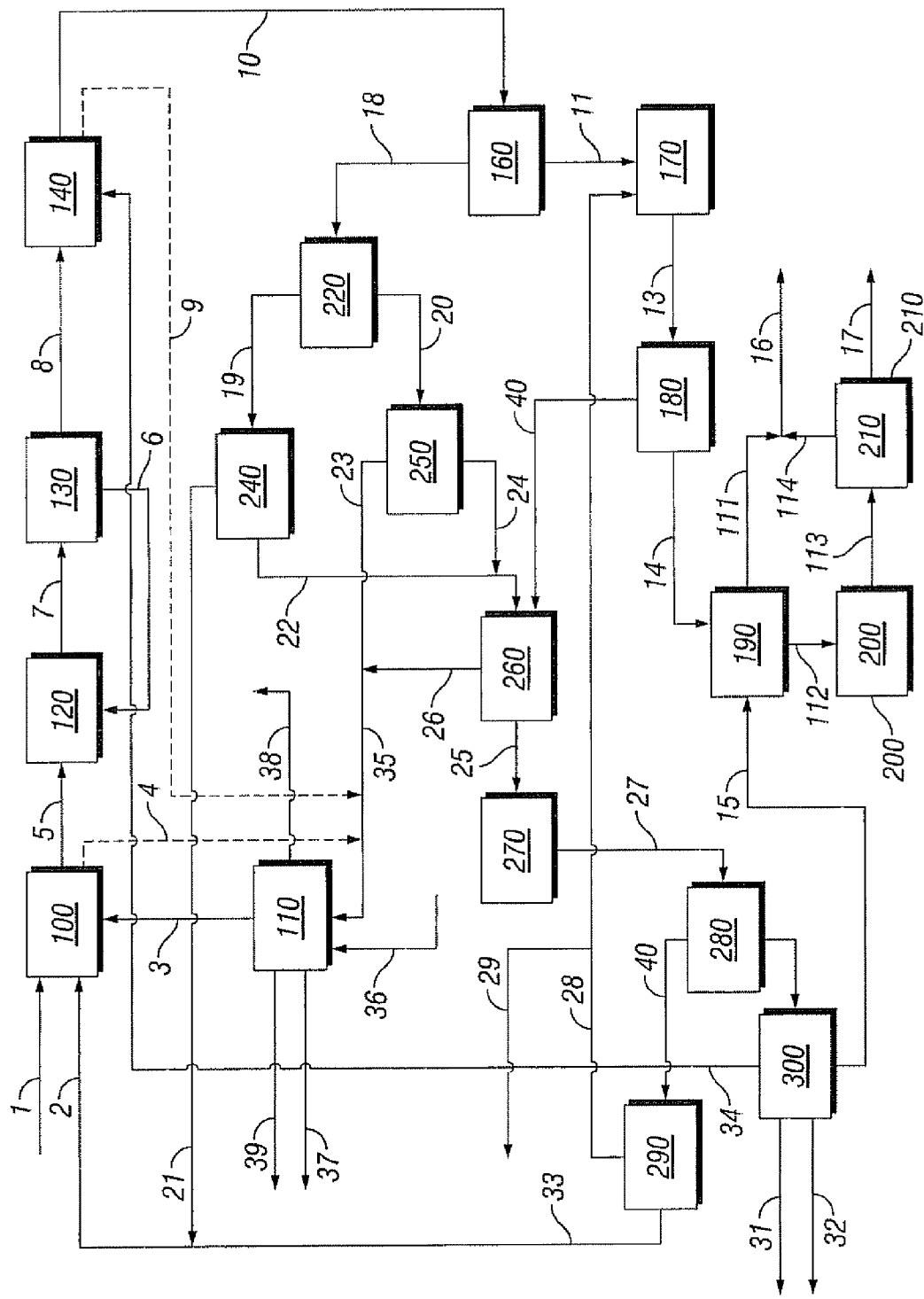
FIG. 1 is a flow diagram illustrating the process of the present invention.

The present invention provides a process for the production of aromatic compounds and ethylene and/or propylene from low molecular weight alkanes, primarily methane. Other alkanes, such as ethane, propane, butane, and pentane, may be mixed in with the methane. First, at least one low molecular weight alkane, preferably methane, is halogenated by reacting it with a halogen, preferably bromine. The monohaloalkane, preferably monobromomethane, which is produced thereby may be contacted with a suitable coupling catalyst which causes the monohaloalkane to react with itself to produce higher molecular weight hydrocarbons such as aromatics and a mixture of intermediate range molecular weight alkanes and likely some alkenes, particularly those having from 2 to 5 carbon atoms. A small amount of methane may also be produced. The aromatic compounds, such as benzene, toluene and xylenes, may be separated from the methane and $C_{2+}$, usually $C_{2-5}$, alkanes and alkenes. After an optional clean-up step to remove residual hydrogen bromide, the $C_{2+}$ alkanes or a portion thereof may then be cracked in an alkane cracking system to produce ethylene and/or propylene. It is possible that $C_{2-3}$ and/or $C_{4+}$ olefins and/or diolefins may be produced. These may be recycled to coupling or cracked in step (d) (after optional hydrogenation). Higher molecular weight aromatic hydrocarbons may also be produced in the coupling step, such as those containing nine or more carbon atoms. These $C_{9+}$ hydrocarbons may be processed as described below and converted into olefins and/or more desirable aromatic hydrocarbons such as benzene, toluene and/or xylenes.

The hydrocarbon feed may be comprised of a low molecular weight alkane. Low molecular weight alkanes include methane, ethane and propane, as well as butane and pentane. The preferred feed is natural gas which is comprised of methane and often contains smaller amounts of ethane, propane and other hydrocarbons. The most preferred feed is methane.

Higher molecular weight hydrocarbons are defined herein as those hydrocarbons having a greater number of carbon atoms than the components of the lower molecular weight hydrocarbon feedstock. Higher molecular weight hydrocarbons include aromatic hydrocarbons, especially benzene, toluene and xylenes (hereinafter referred to as "BTX").

In a preferred embodiment, the coupling reaction may be carried out such that the production of aromatic hydrocarbons, specifically BTX, is maximized. The production of aromatic hydrocarbons may be achieved by the use of a suitable coupling catalyst under suitable operating conditions.

Representative halogens include bromine and chlorine. It is also contemplated that fluorine and iodine may be used but not necessarily with equivalent results. Some of the problems associated with fluorine possibly may be addressed by using dilute streams of fluorine. It is expected that more vigorous reaction conditions will be required for alkyl fluorides to couple and form higher molecular weight hydrocarbons. Similarly, problems associated with iodine (such as the endothermic nature of some iodine reactions) may likely be addressed by carrying out the halogenation and/or coupling reactions at higher temperatures and/or pressures. The use of bromine or chlorine is preferred and the use of bromine is most preferred. While the following description may only refer to bromine, bromination and/or bromomethanes, the description is applicable to the use of other halogens and halomethanes as well.

Bromination of the methane (methane will be used in the following description but other alkanes may be used or may be present as discussed above) may be carried out in an open pipe, a fixed bed reactor, a tube-and-shell reactor or another suitable reactor, preferably at a temperature and pressure where the bromination products and reactants are gases. Fast mixing between bromine and methane is preferred to help prevent over-bromination and coking. For example, the reaction pressure may be from about 100 to about 5000 kPa and the temperature may be from about 150 to about 600° C.,
more preferably from about 350 to about 550° C. and even more preferably from about 400 to about 515° C. Higher temperatures tend to favor coke formation and lower temperatures require larger reactors. Methane bromination may be initiated using heat or light with thermal means being preferred.

A halogenation catalyst may also be used. In an embodiment, the reactor may contain a halogenation catalyst such as a zeolite, amorphous alumino-silicate, acidic zirconia, tungensteastes, solid phosphoric acids, metal oxides, mixed metal oxides, metal halides, mixed metal halides (the metal in such cases being for example nickel, copper, cerium, cobalt, etc.) and/or other catalysts as described in U.S. Pat. Nos. 3,935,289 and 4,971,664, each of which is herein incorporated by reference in its entirety. Specific catalysts include a metal bromide (for example, sodium bromide, potassium bromide, copper bromide, nickel bromide, magnesium bromide and calcium bromide), a metal oxide (for example, silicon dioxide, zirconium dioxide and aluminum trioxide) or metal (for example, platinum, palladium, ruthenium, iridium, or rhodium) to help generate the desired brominated methane.

The bromination reaction product comprises monobromomethane, HBr and also small amounts of dibromomethane and tribromomethane. If desired, the HBr may be removed prior to coupling. The presence of large concentrations of the polybrominated species in the feed to the coupling reactor may decrease bromine efficiency and result in an undesirable increase in coke formation. In many applications, such as the production of aromatics and light olefins, it is desirable to feed only monobromomethane to the coupling reactor to improve the conversion to the final higher molecular weight hydrocarbon products. In an embodiment of the invention, a separation step is added after the halogenation reactor in which the monobromomethane is separated from the other bromomethanes. The di- and tribromomethane species may be recycled to the bromination reactor. One separation method is described in U.S. Published Patent Application No. 2007/02388909, which is herein incorporated by reference in its entirety. Preferably, the separation is carried out by distillation. The di- and tribromomethanes are higher boiling than the monobromomethane, unreacted methane and HBr, which is also made by the bromination reaction:

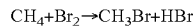

$$CH_4+Br_2 \rightarrow CH_3Br+HBr$$

In a preferred embodiment, the polybromomethanes may be recycled to the halogenation reaction and preferably reproportionated to convert them to monobromomethane. The polybromomethanes contain two or more bromine atoms per molecule. Reproportionation may be accomplished according to U.S. Published Patent Application 2007/0238909 which is herein incorporated by reference in its entirety. Reactive reproportionation is accomplished by allowing the methane feedstock and any recycled alkanes to react with the polybrominated methane species from the halogenation reactor, preferably in the substantial absence of molecular halogen. Reproportionation may be carried out in a separate reactor or in a region of the halogenation reactor.

The bromination and coupling reactions may be carried out in separate reactors or the process may be carried out in an integrated reactor, for example, in a zone reactor as described in U.S. Pat. No. 6,525,230 which is herein incorporated by reference in its entirety. In this case, halogenation of methane may occur within one zone of the reactor and may be followed by a coupling step in which the liberated hydrobromic acid may be adsorbed within the material that catalyzes condensation of the halogenated hydrocarbon. Hydrocarbon coupling may take place within this zone of the reactor and may yield the product higher molecular weight hydrocarbons including aromatic hydrocarbons. It is preferred that separate reactors be used for bromination and coupling because operating conditions may be optimized for the individual steps and this allows for the possibility of removing polybrominated-methane before the coupling step.

Coupling of monobromomethane may be carried out in a fixed bed, fluidized bed or other suitable reactor. The temperature may range from about 150 to about 600° C., preferably from about 300 to about 550° C., most preferably from about 350 to about 475° C., and the pressure may range from about 10 to about 3500 kPa absolute, preferably about 100 to about 2500 kPa absolute. In general, a relatively long residence time favors conversion of reactants to products as well as product selectivity to BTX, while a short residence time means higher throughput and possibly improved economics. It is possible to change product selectivity by changing the catalyst, altering the reaction temperature, pressure and/or altering the residence time in the reactor. Low molecular weight alkanes may also exit the coupling reactor. These low molecular weight alkanes may be comprised of ethane and propane but may also include methane and a small amount of $C_{4-5}$ alkanes and smaller amounts of alkenes. Some of these may be recycled to the bromination reactor but preferably the low molecular weight alkanes may be directed to the cracking step.

Preferred coupling catalysts for use in the present invention are described in U.S. Patent Application No. 2007/0238909 and U.S. Pat. No. 7,244,867, each of which is herein incorporated by reference in its entirety.

A metal-oxygen cataloreactant may also be used to facilitate the coupling reaction. The term "metal-oxygen cataloreactant" is used herein to mean a cataloreactant material containing both metal and oxygen. Such cataloreactants are described in detail in U.S. Published Patent Application Nos. 2005/0038310 and 2005/0171393 which are herein incorporated by reference in their entirety. Examples of metal-oxygen cataloreactants given therein include zeolites, doped zeolites, metal oxides, metal oxide-impregnated zeolites and mixtures thereof. Nonlimiting examples of dopants include alkaline earth metals, such as calcium, magnesium, manganese and barium and their oxides and/or hydroxides.

Hydrogen bromide may also be produced along with monobromomethane in the bromination reactor. The hydrogen bromide may be carried over to the coupling reactor or, if desired, may be separated before coupling. The products of the coupling reaction may include higher molecular weight hydrocarbons, especially BTX and $C_{2+}$ alkanes and likely some alkenes, $C_{9+}$ aromatics and hydrogen bromide. In a preferred embodiment, the hydrogen bromide may be separated from the higher molecular weight hydrocarbon products by distillation.

The coupling reaction product higher molecular hydrocarbons and hydrogen bromide may be sent to an absorption column wherein the hydrogen bromide may be absorbed in water using a packed column or other contacting device. Input water in the product stream may be contacted either in co-current or countercurrent flow with countercurrent flow preferred for its improved efficiency. One method for removing the hydrogen bromide from the higher molecular weight hydrocarbon reaction product is described in U.S. Pat. No. 7,244,867 which is herein incorporated by reference in its entirety. HBr present in the $C_{2+}$ alkanes and alkenes stream or the product stream from the bromination reactor may also be removed therefrom by this method.

In an embodiment, the hydrogen bromide is recovered by displacement as a gas from its aqueous solution in the presence of an electrolyte that shares a common ion or an ion that has a higher hydration energy than hydrogen bromide. Also aqueous solutions of metal bromides such as calcium bromide, magnesium bromide, sodium bromide, potassium bromide, etc. may be used as extractive agents.

In another embodiment, catalytic halogen generation is carried out by reacting hydrogen bromide and molecular oxygen over a suitable catalyst. The oxygen source may be air, pure oxygen or enriched air. A number of materials have been identified as halogen generation catalysts. It is possible to use oxides, halides, and/or oxyhalides of one or more metals, such as magnesium, calcium, barium, chromium, manganese, iron, cobalt, nickel, copper, zinc, etc. After the HBr is separated from the hydrocarbon products, it may be reacted to produce bromine for recycle to the bromination step. Catalysts and methods for regeneration of the bromine are described in detail in U.S. Published Application 2007/0238909 which is herein incorporated by reference in its entirety. Recovery of bromine is also described therein.

In addition to the higher molecular weight hydrocarbons and the hydrogen bromide, other materials may exit from the coupling reactor. These include methane, light ends ($C_{2+}$ alkanes and alkenes) and heavy ends (aromatic $C_{9+}$ hydrocarbons and a small amount of nonaromatic $C_{6+}$ hydrocarbons, usually less than 1%). The methane may be separated from these other materials (e.g., by distillation) and recycled to the bromination reactor. The $C_{2+}$ alkanes, and optionally the alkenes, may be separated from the other materials and introduced into an alkane cracker which produces ethylene and/or propylene and possibly other olefins such as butenes, pentenes, etc. The $C_{2+}$ alkanes and alkenes stream may contain some HBr which may be removed prior to cracking. The $C_{9+}$ aromatic hydrocarbons may be hydrogenated. The hydrogen for hydrogenation may be that produced in the alkane cracker. The resulting hydrogenated $C_{9+}$ stream may be cracked in a conventional cracker to produce additional olefins and/or aromatic hydrocarbons. Alternatively, the $C_{9+}$ aromatic hydrocarbons may be converted to xylenes by reproportionation with toluene, hydrodealkylated to BTX or they may be upgraded by a combination of these two steps.

The cracking steps of the present process may be carried out by thermal or catalytic cracking. One method of thermal cracking is to use a conventional steam cracker. The steam cracker conversion may consist of standard furnaces, compression, gas treating and fractionation.

Thermal and Catalytic Cracking for Lower Olefins Production

Lower olefins, i.e. ethylene and propylene, are produced from lower alkanes (ethane, propane and butane) by either thermal or catalytic cracking processes. The thermal cracking process is typically carried out in the presence of superheated steam and this is by far the most common commercially practiced process. Steam cracking is a thermal cracking process in which saturated hydrocarbons (i.e. ethane, propane, butane or their mixture) are broken down into smaller, unsaturated hydrocarbons, i.e, olefins and hydrogen.

In steam cracking, the gaseous feed is diluted with steam and then briefly heated in a furnace (without the presence of oxygen). Typically, the reaction temperature is very high—around 750 to 950° C.—but the reaction is only allowed to take place very briefly. In modern cracking furnaces, the residence time is even reduced to milliseconds (resulting in gas velocities reaching speeds beyond the speed of sound) in order to improve the yield of desired products. After the cracking temperature has been reached, the gas is quickly quenched to stop the reaction in a transfer line heat exchanger.

The products produced in the reaction depend on the composition of the feed, the hydrocarbon to steam ratio and on the cracking temperature and furnace residence time. The process is typically operated at low pressures, around 140 to 500 kPa depending on the overall process design.

The process also results in the slow deposition of coke, a form of carbon, on the reactor walls. This degrades the efficiency of the reactor so reaction conditions are designed to minimize this. Nonetheless, a steam cracking furnace can usually only run for a few months at a time between de-cokings. De-cokings require the furnace to be isolated from the process and then a flow of steam or a steam/air mixture is passed through the furnace coils at high temperature. This converts the hard solid carbon layer to carbon monoxide and carbon dioxide. Once this reaction is complete, the furnace can be returned to service.

Ethylene and propylene may be separated from the resulting complex mixture by repeated compression and distillation at low temperatures. The areas of an olefin plant are: 1) steam cracking furnaces; 2) primary and secondary heat recovery with quench; 3) a dilution steam recycle system between the furnaces and the quench system; 4) primary compression of the cracked gas (multiple stages of compression); 5) hydrogen sulfide and carbon dioxide removal (acid gas removal); 6) secondary compression (1 or 2 stages); 7) followed by drying of the cracked gas; 8) cryogenic treatment; 9) demethanization—all of the cold cracked gas stream goes to the demethanizer tower (The overhead stream from the demethanizer tower may consist of all the hydrogen and methane that was in the cracked gas stream. Cryogenically treating this overhead stream results in the separation of the hydrogen and the methane. This usually involves liquid methane at a temperature around −150° C. Complete recovery of all the methane is usually critical to the economical operation of an olefin plant); 10) deethanization—the bottom stream from the demethanizer tower may go to the deethanizer tower (The overhead stream from the deethanizer tower consists of all the $C_2$,'s that were in the cracked gas stream. The $C_2$ stream may then be selectively hydrogenated to remove acetylene. It may then go to a $C_2$ splitter. The product ethylene may be taken from the overhead of the tower and the ethane coming from the bottom of the splitter may be recycled to the furnaces to be cracked); 11) depropanization—the bottom stream from the deethanizer tower may go to the depropanizer tower (The overhead stream from the depropanizer tower consists of all the $C_3$'s that were in the cracked gas stream. Prior to sending the $C_3$'s to the $C_3$ splitter this stream may be hydrogenated in order to react out the methylacetylene and propadiene. Then this stream may be sent to the $C_3$ splitter. The overhead stream from the $C_3$ splitter is product propylene and the bottom stream from the $C_3$ splitter is propane which may be sent back to the furnaces for cracking or used as fuel); and 12) optional debutanization—the bottom stream from the depropanizer tower may be fed to the debutanizer tower (The overhead stream from the debutanizer is all of the $C_4$'s that are in the cracked gas stream. The bottom stream from the debutanizer consists of everything in the cracked gas stream that is $C_5$ or heavier. This could be called a light pyrolysis gasoline.).

Since the production of ethylene and propylene is energy intensive, much effort has been dedicated recovering heat from the gas leaving the furnaces. Most of the energy recovered from the cracked gas is used to make high pressure (around 8300 kPa) steam. This steam is in turn used to drive the turbines for compressing cracked gas, the propylene refrigeration compressor, and the ethylene refrigeration compressor.

The light olefin cracking process may also be accomplished in the presence of a catalyst. The advantages are the use of much lower temperatures and possibly the absence of steam. In principle, a higher selectivity to olefins and possibly lower coke make may be achieved. Though it has not been practiced commercially at a world scale plant, catalytic cracking has been an area of interest for a long time. The types of catalysts used include zeolites, clays, aluminosilicates, and others. It should be mentioned that this process is practiced commercially in several oil refineries for high molecular weight hydrocarbons which are cracked over zeolite catalysts in a process unit called FCC (Fluidized Catalytic Cracker). It is more common to produce and recover propylene as a byproduct rather than both ethylene and propylene.

Depending upon the specific combination of process steps described above which are utilized, the present invention may provide some or all of the following advantages:

(1) By not recycling $C_{2-5}$ hydrocarbons to the methane bromination step, the safety issues associated with handling a concentrated stream of multibrominated hydrocarbons are avoided.

(2) A separate bromination/reproportionation reactor for bromination of a $C_{2-5}$ hydrocarbon recycle stream is eliminated.

(3) Coking in the coupling reactor may be reduced significantly and the amount of polybrominated methane which must be removed between the bromination and coupling steps may also be reduced.

(4) Generation of ethylene and/or propylene as products, and optionally other lower olefins, in addition to aromatic hydrocarbons delivers a higher value-added product mix.

(5) Hydrogenation/cracking of the heavy ends further increases the value of the product mix.

(6) Cracking the light ends streams (and optionally the heavy ends streams) may eliminate the production of a fuels stream that would have residual bromine content and the associated atmospheric emissions of hydrogen bromide.

(7) Cracking the light ends (and optionally cracking the heavy ends) may reduce the amount of bromine required per pound of product which in turn may allow reduction of the size of the bromine generation section, thus reducing the capital costs.

(8) Hydrogen needed for reproportionation of $C_{9+}$ aromatics with toluene and hydrodealkylation may be supplied from the cracker instead of by purchase of commercial hydrogen.

(9) Conversion of methane to aromatics is an overall highly exothermic reaction. Alkane cracking is an overall endothermic reaction. Integration of these two processes may allow opportunities for heat integration.

Heat from the conversion of methane to aromatics and light hydrocarbons, including heat generated in the generation of bromine, may be used in the process to supply energy required in alkane cracking, heating the feed streams for the bromination, reproportionation and/or coupling reactions and for heat required in any of the fractionation operations. At least part of the energy released in the conversion of hydrogen bromide to bromine may be recovered and utilized in steps (a)-(d) or any combination thereof and optionally in upstream (including but not limited to gas feedstock processing) and/or downstream processing (including, but not limited to light olefin and BTX conversion and purification, disproportion reactions, aromatic $C_{9+}$ hydrocarbon reproportionation reactions, isomerization reactions, and conversion of ethylene and propylene and BTX to downstream products).

The ethylene, propylene and other olefins which may be produced may then be used to produce many commercial chemical products, for example, polyethylene, polypropylene, ethylene glycol, ethylene oxide, alpha olefins, detergent-range alcohols, propylene glycol, propylene oxide, acrylic acid, ethanol, n-butanol, 2-ethyl-hexanol, etc.

Phenol can be made from the partial oxidation of benzene or benzoic acid, by the cumene process or by the Raschig process. It can also be found as a product of coal oxidation.

The cumene process is an industrial process for developing phenol and acetone from benzene and propylene in which cumene is the intermediate material during the process. This process converts two relatively inexpensive starting materials, benzene and propylene, into two more valuable ones, phenol and acetone. Other reactants required are oxygen from air and small amounts of a radical initiator. Most of the worldwide production of phenol and acetone is now based on this method.

Cumene is the common name for isopropylbenzene. Nearly all the cumene that is produced as a pure compound on an industrial scale is converted to cumene hydroperoxide which is an intermediate in the synthesis of other industrially important chemicals such as phenol and acetone.

Cumene was for many years been produced commercially by the alkylation of benzene with propylene over a Friedel-Crafts catalyst, particularly solid phosphoric acid or aluminum chloride such as described in U.S. Pat. No. 4,343,957. More recently, however, zeolite-based catalyst systems have been found to be more active and selective for propylation of benzene to cumene. It is known that aromatic hydrocarbons can be alkylated in the presence of acid-treated zeolite. U.S. Pat. No. 4,393,262 (1983) teaches that cumene is prepared by the alkylation of benzene with propylene in the presence of a specified zeolite catalyst. U.S. Pat. No. 4,992,606 describes the use of MCM-22 zeolite in the alkylation of benzene with propylene. Other methods are described in U.S. Pat. Nos. 4,441,990, 5,055,627, 6,525,236 and 6,888,037. All of these patents are herein incorporated by reference in their entirety.

In one embodiment, cumene may be produced by contacting benzene with propylene in a distillation column reactor containing a fixed bed acidic catalytic distillation structure comprising a molecular sieve in a distillation reaction zone thereby catalytically reacting the benzene and propylene to produce an alkylated benzene product including cumene. Cumene may be produced in the catalyst bed under 0.25 to 50 atmospheres of pressure and at temperatures in the range of 50° C. to 500° C., using as the catalyst a mole sieve characterized as acidic. Propylene may be fed to the catalyst bed while benzene may be conveniently added through a reflux to result in a molar excess present in the reactor to that required to react with propylene, thereby reacting substantially all of the propylene and recovering benzene as the principal overhead and cumene and diisopropyl benzene in the bottoms. Concurrently, in the fixed bed the resultant alkylated benzene product is fractionated from the unreacted materials and cumene is separated from the alkylated benzene product (preferably by fractional distillation).

The principal alkylated benzene product is cumene. In addition there may be other alkylated products including di and tri isopropyl benzene, n-propyl benzene, ethyl benzene, toluene, diethyl benzene and di-n-propyl benzene, which are believed to be disproportion and isomerization products of cumene. In a preferred process the residual alkylated products remaining after cumene separation may be passed to a transalkylation reactor operated under conditions to transalkylate polyalkylated benzene, e.g., diisopropyl benzene and triisopropyl benzene, to cumene which may be separated from the other materials in the transalkylation product stream and may be combined with the cumene from the first separation.

Cumene may be oxidized in slightly basic conditions in presence of a radical initiator which removes the tertiary benzylic hydrogen from cumene and hence forms a cumene radical. This cumene radical then bonds with an oxygen molecule to give the cumene hydroperoxide radical, which in turn forms cumene hydroperoxide ($C_6H_5C(CH_3)_2$—O—O—H) by abstracting benzylic hydrogen from another cumene molecule. This cumene hydroperoxide converts into cumene radicals and feeds back into subsequent chain formations of cumene hydroperoxides. A pressure of at least about 5 atm may be used to ensure that the unstable peroxide is kept in liquid state.

For example, cumene hydroperoxide may be made according to the process described in U.S. Pat. No. 7,141,703, which is herein incorporated by reference in its entirety. The process comprises providing an oxidation feed consisting essentially of an organic phase. The oxidation feed comprises one or more alkylbenzenes such as cumene and a quantity of neutralizing base having a pH of from about 8 to about 12.5 in 1 to 10 wt. % aqueous solution. The quantity of neutralizing base is effective to neutralize at least a portion of acids formed during the oxidation. The oxidation feed comprises up to an amount of water effective to increase neutralization of acids formed during the oxidation without forming a separate aqueous phase. The oxidation feed is exposed to oxidation conditions effective to produce an oxidation product stream comprising one or more product hydroperoxides.

Cumene hydroperoxide may then be hydrolyzed in an acidic medium to give phenol and acetone.

Additional technologies such as benzene sulfonation/hydrolysis and benzene chlorination/hydrolysis processes may also be used to convert the benzene into phenol, although currently they are not as economically competitive as the cumene process.

The direct oxidation of benzene using air or oxygen is another way in which benzene may be converted into phenol according to the present invention. It does not require reaction with propylene. For example, U.S. Pat. No. 4,992,600, which is herein incorporated by reference in its entirety, describes a process for the oxidation of benzene to phenol which comprises contacting and thereby reacting benzene and oxygen with a (poly)metal salt of a dihydrodihydroxyanthracene(poly)sulfonate having at least one sulfonate moiety on the 2, 3, 6 or 7 position(s) and which salt is dissolved in water, optionally in the presence of an oxidation catalyst, and subsequently separating from the reaction product phenol and the corresponding (poly)metal salt of anthraquinone-(poly)sulfonate. The by-product anthraquinone salt is suitably recycled to the benzene oxidation step by hydrogenating the anthraquinone salt, preferably dissolved in water, to the dihydrodihydroxyanthracene salt by contacting it with hydrogen in the presence of a hydrogenation catalyst.

Additionally, U.S. Pat. No. 6,900,358, which is herein incorporated by reference in its entirety, describes a process for the oxidation of benzene to phenol which comprises continuously contacting, in a distillation column reactor comprising a reaction zone and a distillation zone, benzene with a zeolite catalyst and an oxidant at a temperature in the range of from above 100° C. to 270° C. thereby producing a hydroxylated product, wherein at least a portion of the benzene being in a liquid phase; continuously separating the hydroxylated product from the un-reacted benzene in the distillation zone under conditions effective to vaporize said un-reacted benzene and maintain the hydroxylated product in a liquid phase; and recovering the hydroxylated product from the distillation column reactor.

The integrated process of this invention may also include the reaction of benzene with olefins such as ethylene. The ethylene may be produced separately in an ethane dehydrogenation unit or may come from olefin cracker process vent streams or other sources.

Ethylbenzene is an organic chemical compound which is an aromatic hydrocarbon. Its major use is in the petrochemical industry as an intermediate compound for the production of styrene, which in turn is used for making polystyrene, a commonly used plastic material. Although often present in small amounts in crude oil, ethylbenzene is produced in bulk quantities by combining the petrochemicals benzene and ethylene in an acidically-catalyzed chemical reaction. Catalytic dehydrogenation of the ethylbenzene then gives hydrogen gas and styrene, which is vinylbenzene. Ethylbenzene is also an ingredient in some paints.

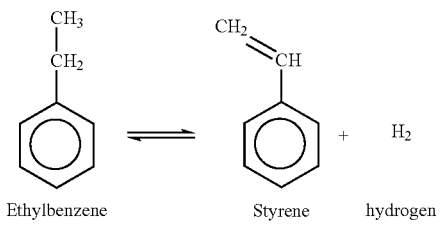

Ethylbenzene may, for example, be produced according to the process of U.S. Pat. No. 5,243,116, which is herein incorporated by reference in its entirety. The process comprises alkylating benzene by contacting the benzene with ethylene in the presence of a catalyst consisting essentially of an acidic mordenite zeolite having a silica/alumina molar ratio of at least 30:1 and a crystalline structure which is determined by X-ray diffraction to be a matrix of Cmcm symmetry having dispersed therein domains of Cmmm symmetry and having a Symmetry Index of at least about 1.

Another process for producing ethylbenzene from benzene is described in U.S. Pat. No. 5,877,370, which is herein incorporated by reference in its entirety. The process comprises passing benzene, ethylene, and a diluent comprising at least one phenyl group and at least one ethyl group to an alkylation zone; reacting the benzene and the ethylene in the alkylation zone in the presence of zeolite beta to alkylate the benzene to form ethylbenzene; and withdrawing from the alkylation zone a product comprising ethylbenzene.

Styrene may then be produced by dehydrogenating the ethylbenzene. One process for producing styrene is described in U.S. Pat. No. 4,857,498, which is herein incorporated by reference in its entirety. Another process for producing styrene is described in U.S. Pat. No. 7,276,636, which is herein incorporated by reference in its entirety. This process for producing styrene comprises: a) reacting benzene and a polyethylbenzene in a transalkylation reactor to form ethylbenzene; b) dehydrogenating ethylbenzene in a dehydrogenation reactor to form styrene; c) withdrawing a dehydrogenation reactor effluent comprising styrene from the dehydrogenation reactor, and passing at least a portion of the dehydrogenation reactor effluent to a dehydrogenation separation section; d) recovering styrene from the dehydrogenation separation section; e) introducing a first inhibitor element component to the dehydrogenation separation section; f) recovering from the dehydrogenation separation section a recycle stream comprising a second inhibitor element component; and g) passing at least 33% of the second inhibitor element component recovered in f) to the transalkylation reactor.

One embodiment of the invention is illustrated in FIG. 1. Methane derived from natural gas purification is delivered through line 1 to the bromination reactor 100 at 30 barg (3000 kPag) and ambient temperature. This methane stream is combined with methane recycle stream 2, heated to 450° C., and fed to the bromination reactor 100. Bromine liquid is pumped from storage in line 3, vaporized and heated to 250° C., and fed in a staged manner into to the bromination reactor 100.

In the bromination reactor 100, bromine reacts adiabatically with methane to form methyl bromide, methyl dibromide, methyl tribromide, and hydrogen bromide. In this example, the reactor does not utilize a catalyst. During normal operation, a small amount of coke is produced. The bromination reactor 100 is comprised of at least 2 parallel reactor trains to allow for one train to be decoked while the other train(s) remains in normal operation. Reactor effluent gas from the decoking operation is routed through line 4 to the bromine generation reactor 110 (described below).

A gas mixture containing methyl bromides, hydrogen bromide and unreacted methane, exits the bromination reactor 100 through line 5 at 510° C. and 30 barg (3000 kPag) and enters the reproportionation reactor 120. The reproportionation product gas stream 7 is cooled and fractionated in a conventional distillation column 130 to separate polybromides from the other reproportionation products. Polybrominated hydrocarbons, recovered from distillation column 130, are fed to the reproportionation reactor 120 through line 6 where di- and tri-substituted methyl bromide and other polybrominated hydrocarbons react adiabatically with unreacted methane to form monobromomethane. In this example, the reproportionation reactor 120 does not utilize a catalyst.

The remaining components of the reproportionation product stream 7 (primarily monobromomethane, hydrogen bromide, and unreacted methane) are recovered as a separate stream 8, vaporized, reheated to 400° C., and fed to the coupling reactor 140.

In the coupling reactor 140, monobromomethane reacts adiabatically over a catalyst, preferably manganese-based, at a temperature of 425° C. and 25 barg (2500 kPag) to produce a mixture of compounds comprised predominately of benzene, toluene, xylenes, ethane, propane, butane, and pentanes. The coupling reactor 140 may be comprised of multiple fixed bed catalytic reactors operating on a reaction/regeneration cycle. During the reaction phase, monobromomethane reacts to form mixed products. At the same time, coke is formed and gradually deactivates the catalyst. During the regeneration phase of a reactor, reactor feed is redirected to one of the reactor vessels which is in the reaction phase of the cycle. Heated air is utilized to burn coke and regenerate the catalyst. Reactor effluent gas is routed through line 9 to the bromine generation reactor 110.

Product gas from the coupling reactor 140 is directed through line 10 and cooled and fractionated in conventional distillation column 160 to produce two streams. The higher boiling stream, 11, is comprised primarily of benzene, toluene, and xylenes. The lower boiling stream, 18, is comprised primarily of methane, ethane, propane, butanes, pentanes, and hydrogen bromide.

The higher boiling stream 11 from distillation column 160 is heated and routed to product cleanup reactor 170. Hydrogen from line 28 is added to this adiabatic trickle phase reactor which uses a palladium-based catalyst to convert residual hydrocarbon bromides to the equivalent alkanes and hydrogen bromide.

Stream 13 exiting the product cleanup reactor 170 is fractionated in conventional distillation column 180 to recover bromine-free stream 14 which is comprised primarily of benzene, toluene, and xylenes (BTX) and a second lights stream 40 which is comprised primarily of hydrogen bromide, unreacted hydrogen, and light hydrocarbons (produced by dehalogenation in product cleanup reactor 170).

BTX stream 14 is combined with a $C_{6+}$ stream 15 generated by steam cracking (described below) and fed to conventional distillation column 190 to produce benzene in stream 111. The non-benzene fraction from column 190, comprised of toluene and mixed xylenes, is fed through line 112 to a conventional disproportionation unit 200 to produce roughly eqimolar benzene and xylenes in line 113 which are separated in separator 210. The benzene stream 114 is combined with the product benzene stream 111 to form benzene product stream 16 (or optionally fed to column 180 if additional purification is required). The mixed xylenes are converted to para-xylene via conventional technology (Perex—recovering the para-xylene from the xylene mixture, followed by re-isomerization of the para-isomer-deprived mixed xylenes to an equilibrium mixture, and repeating the cycle of recovery and isomerization) and leave as product stream 17. Light and heavy ends from benzene purification, disproportionation, and xylenes conversion and distillation are used in the process as fuel or recycled (e.g. as feed to the steam cracker). Benzene and para-xylene are stored and sold as products.

The lower boiling stream 18 from column 160 is comprised of hydrogen bromide and $C_{1-5}$ hydrocarbons, primarily alkanes. This stream 18 is fractionated in distillation column 220 to produce a stream 19 that is comprised primarily of $C_1$ and $C_2$ hydrocarbons, primarily methane and ethane and a second stream 20 that is comprised of hydrogen bromide and $C_{3-5+}$ hydrocarbons (primarily propane, butanes, and pentanes). The $C_1$ and $C_2$ hydrocarbon stream 19 is fractionated in column 240 to produce methane, which is recycled to bromination reactor 100 through line 21, and an ethane/ethylene stream 22. The second stream 20 is fractionated in column 250 to produce a tops stream 23 containing hydrogen bromide, which is routed to bromine generation reactor 110, and a bottoms stream 24 containing $C_{3-5+}$ hydrocarbons.

The $C_{3-5+}$ hydrocarbon stream 24 is combined with ethane/ethylene stream 22 and lights stream 40 and sent to water scrubber 260 to remove small residual amounts of hydrogen bromide. Hydrogen bromide is recovered in line 26 and sent to bromine generation reactor 110. The combined $C_{2-5+}$ mixed hydrocarbon fraction 25 is fed to steam cracker 270.

Steam cracker 270 uses conventional furnace technology to crack the mixed hydrocarbon feed 25 to produce primarily ethylene, propylene, hydrogen, methane, butylene, $C_{5s}$, benzene, and other $C_{6s}$ in line 27. Downstream of the furnaces, standard cracker product separation technology is employed to separate hydrogen 28 for use in the product cleanup reactor 170 and for export through line 29 and/or for an optional hydro-dealkylation reactor (not shown) if that technology is used to convert toluene into benzene.

The standard cracker product separation technology employed herein comprises the separation of methane and hydrogen from $C_{2-5+}$ hydrocarbons in column 280. Methane and hydrogen are directed to column 290 through line 40. Methane is separated from hydrogen in column 290. Methane in line 33 is recycled to bromination reactor 100.

$C_{2-5+}$ hydrocarbons are fractionated in fractionator 300 to produce $C_{4-5}$ fraction 34 which is recycled to coupling reactor 140, $C_{6+}$ fraction 15 which is routed to BTX fractionation 190 and ethylene and propylene which are separated, purified, and exported as products, ethylene in line 31 and propylene in line 32.

Hydrogen bromide in line 23 from column 250 and in line 26 from scrubber 260 is combined in line 35 and is heated and fed to the bromine generation reactor 110. Air is compressed and fed through line 36 to bromine generation reactor 110 and the catalyst is continuously regenerated. Regeneration gas from coupling reactor 140 (line 9) and bromination reactor decoker 4 is also fed to bromine generation reactor 110. Bromine generation reactor 110 may be comprised of several shell/tube exchangers whose tubes are filled with copper oxide catalyst. Heat released by the exothermic conversion of hydrogen bromide to bromine is removed by generation of steam (line 37) and may be subsequently utilized elsewhere in the process (e.g. in the fractionation steps). The effluent from reactor 110 is further cooled, generating additional steam. The inert gases, primarily nitrogen and unreacted oxygen are routed to a bromine scavenging adsorbent (not shown) and then released through line 38. The liquid product from bromine generation reactor 110, comprised of water and bromine, is phase separated at sub-ambient temperature and then distilled to produce a water stream 39 and a bromine stream 3 which is dried and recycled to bromination reactor 100. The water stream 39 is further purified and released.

EXAMPLE 1

Referring to FIG. 1, the flow rate in methane feed line 1 to the bromination reactor 100 is 100 kg/hr, the flow rate in methane recycle line 2 is 73 kg/hr and the flow rate in the bromine feed line 3 is 1164 kg/hr. Reactor 100 is operated at 510° C. and 3000 kPa. The conversion of methane is 50% and the selectivity to monobromomethane is 67%.

Reproportionation reactor 120 is also operated at 510° C. and 3000 kPa. The conversion is 43% and the selectivity to monobromomethane is 100%. Coupling reactor 140 is operated at 425° C. and 2500 kPa. The conversion of the monobromomethane is 100% and the selectivity to BTX is 32%.

Bromine generation reactor 110 is operated at 375° C. and 200 kPa and the flow rate of air through feed line 36 is 554 kg/hr. The conversion and selectivity are both 100%. The flow rate in water stream 39 is 131 kg/hr.

Steam cracker 270 is operated at 840° C. and 100 kPa. The conversion of the monobromomethane is 84% and the selectivity to lower olefins is 60%.

14 kg/hr of benzene and 23 kg/hr of p-xylene are produced. 25 kg/hr of ethylene and 12 kg/hr of propylene are produced.

What is claimed is:

1. An integrated process for producing aromatic hydrocarbons and ethylene and/or propylene from low molecular weight alkanes, which comprises:
   (a) contacting at least one low molecular weight alkane with a halogen, under process conditions sufficient to produce a monohaloalkane,
   (b) reacting the monohaloalkane in the presence of a coupling catalyst to produce aromatic hydrocarbons and $C_{2+}$ alkanes,
   (c) separating the aromatic hydrocarbons from the product mixture of step (b) to produce aromatic hydrocarbons, and
   (d) cracking at least part of the $C_{2+}$ alkanes in an alkane cracking system to produce ethylene and/or propylene.

2. The process of claim 1 wherein $C_{2-5}$ alkenes are also produced in step (b) and $C_{4+}$ alkanes and alkenes are separated from $C_{2-3}$ alkanes and alkenes, the $C_{4+}$ alkanes and alkenes are optionally recycled to step (b), the $C_{2-3}$ alkanes are optionally separated from $C_{2-3}$ alkenes and at least part of the $C_{2-3}$ alkanes are cracked in step (d).

3. The process of claim 1 or 2 wherein aromatic $C_{9+}$ hydrocarbons are also produced in step (b) and are separated from the other products of step (b), hydrogenated and then subjected to hydrocarbon cracking to produce olefins and/or aromatic hydrocarbons.

4. The process of claim 3 wherein at least part of the hydrogen used for the hydrogenation of the aromatic $C_{9+}$ hydrocarbons is produced in step (d).

5. The process of claim 1 or 2 wherein aromatic $C_{9+}$ hydrocarbons are also produced in step (b) and are separated from the other products of step (b) and reproportionated to xylenes with toluene and/or hydrodealkylated to produce benzene, toluene and/or xylenes.

6. The process of claim 5 wherein at least part of the hydrogen used for the reproportionation and/or hydrodealkylation is produced in step (d).

7. The process of claim 1 or 2 wherein at least some unconverted methane and/or at least some of any produced methane is recovered and recycled to step (a).

8. The process of claim 1 or 2 wherein at least some ethane and/or propane produced in step (b) is recycled to step (a).

9. The process of claim 1 or 2 wherein multi-halogenated alkane species made in step (a) are separated from the monohaloalkane prior to step (b).

10. The process of claim 9 wherein the multi-halogenated species are recycled.

11. The process of claim 10 wherein the multi-halogenated species are reproportionated to form more monohaloalkane.

12. The process of claim 1 or 2 wherein at least some hydrogen bromide is present in the $C_{2+}$ alkanes and is removed prior to step (d).

13. The process of claim 1 or 2 wherein the low molecular weight alkane is comprised of methane and the halogen is comprised of bromine.

14. The process of claim 1 or 2 wherein hydrogen bromide is produced in the process.

15. The process of claim 14 wherein at least some of the hydrogen bromide is converted to bromine which is optionally recycled to step (a).

16. The process of claim 15 wherein at least part of the energy released in the conversion of hydrogen bromide to bromine is recovered and utilized in steps (a)-(d) or any combination thereof and optionally in upstream and/or downstream processing.

17. The process of claim 1 or 2 wherein the aromatic hydrocarbons comprise at least in part a xylene mixture and para-xylene is produced by the steps of 1) recovering para-xylene from the xylene mixture, 2) re-isomerizing the para-xylene-deprived xylene mixture to an equilibrium mixture, and 3) repeating steps 1) and 2).

18. A process for producing phenol which comprises producing benzene according to the process of claim 1 or 2 and then either:
  1) reacting benzene with propylene to produce cumene, oxidizing the cumene to produce cumene hydroperoxide and then hydrolyzing the cumene hydroperoxide in an acidic medium to produce phenol, or
  2) directly oxidizing benzene using air or oxygen, or
  3) sulfonating the benzene and then hydrolyzing the sulfonate product, or
  4) chlorinating the benzene and the hydrolyzing the chlorinated product to produce phenol.

19. A process for producing styrene which comprises producing benzene according to the process of claim 1 or 2, reacting the benzene with ethylene to produce ethylbenzene and then dehydrogenating the ethylbenzene to produce styrene.

* * * * *